(12) United States Patent
De Haan (10) Patent No.: US 10,349,900 B2
(45) Date of Patent: Jul. 16, 2019

(54) DEVICE, SYSTEM AND METHOD FOR EXTRACTING PHYSIOLOGICAL INFORMATION

(71) Applicant: KONINKLIJKE PHILIPS N.V., Eindhoven (NL)

(72) Inventor: Gerard De Haan, Helmond (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 527 days.

(21) Appl. No.: 14/703,008

(22) Filed: May 4, 2015

(65) Prior Publication Data

US 2015/0320363 A1 Nov. 12, 2015

Related U.S. Application Data

(60) Provisional application No. 61/990,141, filed on May 8, 2014.

(30) Foreign Application Priority Data

May 7, 2014 (EP) .................................... 14167417

(51) Int. Cl.
*A61B 5/00* (2006.01)
*A61B 5/1455* (2006.01)
(Continued)

(52) U.S. Cl.
CPC .......... *A61B 5/7278* (2013.01); *A61B 5/0077* (2013.01); *A61B 5/0261* (2013.01);
(Continued)

(58) Field of Classification Search
CPC ... A61B 5/7278; A61B 5/0077; A61B 5/7207; A61B 5/02416; A61B 5/0261;
(Continued)

(56) References Cited

U.S. PATENT DOCUMENTS 6,115,502 A * 9/2000 De Haan ................. H04N 5/21
348/618
8,423,116 B2 4/2013 Balberg et al.
(Continued)

FOREIGN PATENT DOCUMENTS

WO 2012158840 A1 11/2012
WO 2014024104 A1 2/2014

OTHER PUBLICATIONS

Corral Martinez, L. F., et al.; Optimal wavelength selection for noncontact reflection photoplethysmography; 2011; Proc. SPIE 8011, 22nd Congress of the International Commission for Optics: Light for the Development of the World; 801191.
(Continued)

*Primary Examiner* — Navin Natnithithadha
*Assistant Examiner* — Andrey Shostak (57) ABSTRACT

A device for extracting physiological information indicative of at least one vital sign of a subject from detected electromagnetic radiation transmitted through or reflected from a subject comprises an input interface for receiving a data stream of detection data derived from detected electromagnetic radiation transmitted through or reflected from a skin region of a subject. The detection data comprises wavelength-dependent reflection or transmission information in at least two signal channels representative of respective wavelength portions. A signal mixer dynamically mixes the at least two signal channels into at least one mixed signal. A processor derives physiological information indicative of at least one vital sign from the at least one mixed signal, and a controller controls the signal mixer to limit the relative contributions of the at least two signal channels mixed into at least one mixed signal and/or the rate-of-change at which said relative contributions are allowed to dynamically change.

10 Claims, 4 Drawing Sheets

(51) Int. Cl.
*A61B 5/0295* (2006.01)
*A61B 5/024* (2006.01)
*A61B 5/026* (2006.01)

(52) U.S. Cl.
CPC ........ *A61B 5/0295* (2013.01); *A61B 5/02416* (2013.01); *A61B 5/1455* (2013.01); *A61B 5/14552* (2013.01); *A61B 5/721* (2013.01); *A61B 5/7207* (2013.01); *A61B 2562/0238* (2013.01); *A61B 2576/00* (2013.01)

(58) Field of Classification Search
CPC ..... A61B 5/1455; A61B 5/0295; A61B 5/721; A61B 5/14552; A61B 2562/0238; A61B 2576/00
See application file for complete search history.

(56) References Cited

U.S. PATENT DOCUMENTS

| | | | |
|---|---|---|---|
| 2002/0045806 A1* | 4/2002 | Baker, Jr. | A61B 5/02416 600/309 |
| 2006/0094943 A1* | 5/2006 | Van Slyke | A61B 5/14551 600/323 |
| 2007/0219439 A1 | 9/2007 | Vilser et al. | |
| 2010/0198087 A1* | 8/2010 | Takahashi | A61B 5/02438 600/500 |
| 2011/0251493 A1* | 10/2011 | Poh | G06K 9/00255 600/477 |
| 2012/0184830 A1 | 7/2012 | Balberg et al. | |
| 2012/0302846 A1* | 11/2012 | Volmer | A61B 5/02416 600/324 |
| 2013/0271591 A1 | 10/2013 | Van Leest et al. | |
| 2013/0294505 A1 | 11/2013 | Kirenko et al. | |
| 2014/0206965 A1 | 7/2014 | De Haan et al. | |
| 2014/0213861 A1 | 7/2014 | Van Leest | |
| 2016/0015308 A1* | 1/2016 | Kirenko | A61B 5/721 600/301 |

OTHER PUBLICATIONS

Lewandowska, M., et al.; Measuring Pulse Rate with a Webcam—a Non-contact Method for Evaluating Cardiac Activity; 2011; Proc. of the Federated Conf. on Computer Science and Information Systems; pp. 405-410.

Poh, M-Z., et al.; Non-contact, automated cardiac pulse measurements using video imaging and blind source separation; 2010; Optics Express; 18(10)10762-10774.

Rustand, A.; Ambient-Light Photoplethysmography; 2012; Thesis for Master of Science in Electronics; Norwegian University of Science and Technology; pp. 1-81.

Verkruysse, W., et al.; Remote plethysmographic imaging using ambient light; 2008; Optical Express; 16(26)21434-21445.

Wieringa, F. P., et al.; Contactless Multiple Wavelength Photoplethysmographic Imaging: A First Step Toward "SpO2 Camera" Technology; 2005; Annals of Biomedical Engineering; 33(8)1034-1041.

G. de Haan and A. van Leest, "Improved motion robustness of remote-PPG by using the blood volume pulse signature", Physiol. Meas. 35 1913, 2014.

* cited by examiner

DEVICE, SYSTEM AND METHOD FOR EXTRACTING PHYSIOLOGICAL INFORMATION

CROSS REFERENCE TO RELATED APPLICATIONS

This application claims the benefit of U.S. provisional application Ser. No. 61/990,141 filed May 8, 2014 and EP provisional application serial no. 14167417.6 filed May 7, 2014, both which are incorporated herein by reference.

FIELD OF THE INVENTION

The present invention relates to a device, system and method for extracting physiological information indicative of at least one vital sign of a subject from detected electromagnetic radiation transmitted through or reflected from a subject, such as a person or animal.

BACKGROUND OF THE INVENTION

Vital signs of a person, for example the heart rate (HR), the respiration rate (RR) or the arterial blood oxygen saturation, serve as indicators of the current state of a person and as powerful predictors of serious medical events. For this reason, vital signs are extensively monitored in inpatient and outpatient care settings, at home or in further health, leisure and fitness settings.

One way of measuring vital signs is plethysmography. Plethysmography generally refers to the measurement of volume changes of an organ or a body part and in particular to the detection of volume changes due to a cardio-vascular pulse wave traveling through the body of a subject with every heartbeat.

Photoplethysmography (PPG) is an optical measurement technique that evaluates a time-variant change of light reflectance or transmission of an area or volume of interest. PPG is based on the principle that blood absorbs light more than surrounding tissue, so variations in blood volume with every heart beat affect transmission or reflectance correspondingly. Besides information about the heart rate, a PPG waveform can comprise information attributable to further physiological phenomena such as the respiration. By evaluating the transmittance and/or reflectivity at different wavelengths (typically red and infrared), the blood oxygen saturation can be determined.

Conventional pulse oximeters (also called contact PPG device herein) for measuring the heart rate and the (arterial) blood oxygen saturation (also called SpO2) of a subject are attached to the skin of the subject, for instance to a fingertip, earlobe or forehead. Therefore, they are referred to as 'contact' PPG devices. A typical pulse oximeter comprises a red LED and an infrared LED as light sources and one photodiode for detecting light that has been transmitted through patient tissue. Commercially available pulse oximeters quickly switch between measurements at a red and an infrared wavelength and thereby measure the transmittance of the same area or volume of tissue at two different wavelengths. This is referred to as time-division-multiplexing. The transmittance over time at each wavelength gives the PPG waveforms for red and infrared wavelengths. Although contact PPG is regarded as a basically non-invasive technique, contact PPG measurement is often experienced as being unpleasant and obtrusive, since the pulse oximeter is directly attached to the subject and any cables limit the freedom to move and might hinder a workflow.

Fast and reliable detection and analysis of a pulse signal and oxygen saturation level (SPO2) is one of the most important activities in many healthcare applications, which becomes crucial if a patient is in a critical condition. In those situations, pulsatility of a heart beat signal is very weak, and therefore, the measurement is vulnerable to any sort of artifacts.

Modern photoplethysmography sensors do not always provide fast and reliable measurement in critical situations. For instance, contact finger pulse oximeters (based on transmissive PPG) are vulnerable to motion of a hand, and fails in case of centralization of a patient due to lower blood volumes on body peripherals. Contact forehead pulse oximeter sensors (using a reflective PPG measurement mode) are supposed to be more robust to a centralization effect. However, the accuracy, robustness and responsiveness of a forehead sensor depends heavily on correct positioning of a sensor on a forehead and proper pressure applied to a skin (too tight application of a sensor might reduce a local blood pulsatility, too loose application might lead to non-reliable measurements due to motion artifacts and/or venous pulsatility).

Recently, non-contact, remote PPG (rPPG) devices (also called camera rPPG device herein) for unobtrusive measurements have been introduced. Remote PPG utilizes light sources or, in general radiation sources, disposed remotely from the subject of interest. Similarly, also a detector, e.g., a camera or a photo detector, can be disposed remotely from the subject of interest. Therefore, remote photoplethysmographic systems and devices are considered unobtrusive and well suited for medical as well as non-medical everyday applications. However, remote PPG devices typically achieve a lower signal-to-noise ratio.

Verkruysse et al., "Remote plethysmographic imaging using ambient light", Optics Express, 16(26), 22 Dec. 2008, pp. 21434-21445 demonstrates that photoplethysmographic signals can be measured remotely using ambient light and a conventional consumer level video camera, using red, green and blue colour channels.

Wieringa, et al., "Contactless Multiple Wavelength Photoplethysmographic Imaging: A First Step Toward "SpO2 Camera" Technology," Ann. Biomed. Eng. 33, 1034-1041 (2005), discloses a remote PPG system for contactless imaging of arterial oxygen saturation in tissue based upon the measurement of plethysmographic signals at different wavelengths. The system comprises a monochrome CMOS-camera and a light source with LEDs of three different wavelengths. The camera sequentially acquires three movies of the subject at the three different wavelengths. The pulse rate can be determined from a movie at a single wavelength, whereas at least two movies at different wavelengths are required for determining the oxygen saturation. The measurements are performed in a darkroom, using only one wavelength at a time.

Using PPG technology, vital signs can be measured, which are revealed by minute light absorption changes in the skin caused by the pulsating blood volume, i.e. by periodic color changes of the human skin induced by the blood volume pulse. As this signal is very small and hidden in much larger variations due to illumination changes and motion, there is a general interest in improving the fundamentally low signal-to-noise ratio (SNR). There still are demanding situations, with severe motion, challenging environmental illumination conditions, or high required accuracy of the application, where an improved robustness and accuracy of the vital sign measurement devices and methods is required, particularly for the more critical healthcare applications Typically the vital sign results from a dynamically varying mix of at least two color (sometimes including infrared) channels. The mix can be found using various techniques, such as blind source separation techniques, and a selection algorithm, or with an energy minimization, minimizing the signal energy in all but a predefined color direction determined by the blood absorption spectrum. Such a method is e.g. described in G. de Haan and V. Jeanne, "Robust pulse-rate from chrominance-based rPPG", IEEE Transactions on Biomedical Engineering, Vol. 60, No. 10, October, 2013, pp. 2878-2886, which is herein incorporated by reference.

SUMMARY OF THE INVENTION

It is an object of the present invention to provide a device, system and a method for extracting physiological information indicative of at least one vital sign of a subject from detected electromagnetic radiation, which provide an increased SNR, accuracy and reliability of the obtained vital sign(s).

In a first aspect of the present invention, a device for extracting physiological information indicative of at least one vital sign of a subject from detected electromagnetic radiation transmitted through or reflected from a subject is presented, the device comprising:

an input interface configured to receive a data stream of detection data derived from detected electromagnetic radiation transmitted through or reflected from a skin region of a subject, wherein the detection data comprises wavelength-dependent reflection or transmission information in at least two signal channels representative of respective wavelength portions, a signal mixer configured to dynamically mix the at least two signal channels into at least one mixed signal, a processor configured to derive physiological information indicative of at least one vital sign from the at least one mixed signal, and a controller configured to control the signal mixer to limit the relative contributions of the at least two signal channels mixed into at least one mixed signal and/or the rate-of-change at which said relative contributions are allowed to dynamically change.

In a further aspect of the present invention, a system for extracting physiological information indicative of at least one vital sign of a subject from detected electromagnetic radiation transmitted through or reflected from a subject is presented, the system comprising:

a detector configured to detect electromagnetic radiation transmitted through or reflected from a skin region of a subject and to derive detection data from the detected electromagnetic radiation, wherein the detection data comprises wavelength-dependent reflection or transmission information in at least two signal channels representative of respective wavelength portions, and a device as disclosed herein for extracting physiological information from said detection data.

In yet further aspects of the present invention, there are provided a corresponding method, a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, system, computer program and medium have similar and/or identical preferred embodiments as the claimed device and as defined in the dependent claims.

It has been observed by the inventors that the known methods for obtaining vital signs from detected electromagnetic radiation produce a stable mixture mainly (or even only) in case of a minimum level of distortions, usually caused by motion of the subject. In very stationary subjects, counter-intuitively the SNR of the vital sign drops, due to the unstable mixture. The present invention aims at improving the SNR of the vital sign, particularly in these near stationary cases.

The present invention is based on the idea to limit the mixture and/or its rate of change, particularly when a low energy is observed in the color channels or a derived signal, as proposed in an embodiment. Limiting the rate of change has the advantage that it still allows all possible mixtures. The invention is equally applicable to various or even all known methods for obtaining the mixed signal(s), e.g. methods using blind source separation (BSS), such as principal component analysis (PCA) or independent component analysis (ICA), methods based on chrominance signals (CHRO-method (CHROM) as disclosed in the above mentioned paper of G. de Haan et al.), methods based on energy minimization in all dimensions but a predefined one (also called PBV-method), and BSS-methods using guidance from PBV or CHRO. These methods will be explained in more detail below.

These method can be interpreted as providing the mixed signal as a mixture of at least two signal channels representative of respective wavelength portions, for instance as a mixture of three signal channels representing red, green and blue signals from a color video camera, but they differ in the way to determine the optimal weighting scheme used for mixing the at least two signal channels. Generally, the resulting weights are aimed at a mixture in which the distortions disappear, i.e. the "weighting vector" is substantially orthogonal to the main distortions, as usually caused by subject motion. According to the present invention, this commonly used weighting scheme is not used, but a more sophisticated control of the signal mixer is applied, according to which limitations are, particularly under certain conditions applied to the mixing and/or the rate-of-change to improve the SNR.

In a preferred embodiment the controller is configured to limit the relative contributions and/or the rate-of-change only in case the energy of the at least two signal channels or a derived measure is below an energy threshold. As explained above, in this case the conventional mixing leads to a reduced SNR. Above the energy threshold the mixing is preferably performed conventionally, i.e. without any limiting so that also above the energy threshold the best SNR can be obtained. The energy threshold may be predetermined (e.g. in a calibration measurement), adaptable, e.g. by the user, or self-learning.

In another embodiment said input interface is configured to receive a motion signal indicating motion of the subject or part of the subject and wherein said controller is configured to limit the relative contributions and/or the rate-of-change only in case the motion is below a motion threshold. The motion signal may be acquired in various ways, e.g. by use of one or more body sensors attached to the subject's body (e.g. accelerometers), by use of motion sensor arranged or in or at a device that is in contact with the subject (e.g. pressure sensors within a mattress), or by use of information obtained from images of the subject. Above the motion threshold the mixing is preferably performed conventionally. The motion threshold, like the energy threshold, may be predetermined (e.g. in a calibration measurement), adaptable, e.g. by the user, or self-learning.

Advantageously, the controller is configured to limit the relative contributions and/or the rate-of-change to a predetermined value or range. The predetermined value or range may e.g. be obtained in a calibration measurement as well. The setting of a predetermined value or range for the relative contributions and/or the rate-of-change allows to optimally control to obtain an increased SNR.

Preferably, said controller is configured to limit the rate-of-change by updating, in particular by recursively updating, the relative contributions. This may be realized by updating weighting factors by which the relative contributions are multiplied for the mixing.

In another embodiment the at least two signal channels are selected from a wavelength interval between 300 nm and 1000 nm, in particular represent the wavelength portions corresponding to red, green and blue light. This is particularly used when the PPG signals are obtained from image signals acquired by a (e.g. conventional) video camera and when the above mentioned principles of remote PPG are used for deriving one or more vital signs. In other embodiments infrared light may also be used in addition or instead of another color channel. For instance, for night-time applications one or more infrared wavelengths may be used in addition or alternatively.

Generally, the interaction of electromagnetic radiation, in particular light, with biological tissue is complex and includes the (optical) processes of (multiple) scattering, backscattering, absorption, transmission and (diffuse) reflection. The term "reflect" as used in the context of the present invention is not to be construed as limited to specular reflection but comprises the afore-mentioned types of interaction of electromagnetic radiation, in particular light, with tissue and any combinations thereof.

The term "vital sign" as used in the context of the present invention refers to a physiological parameter of a subject (i.e. a living being) and derivative parameters. In particular, the term "vital sign" comprises blood volume pulse-signal, heart rate (HR) (sometimes also called pulse rate), heart rate variability (pulse rate variability), pulsatility strength, perfusion, perfusion indicator, perfusion variability, Traube Hering Mayer waves, respiratory rate (RR), skin temperature, blood pressure, a concentration of a substance in blood and/or tissue, such as (arterial) blood oxygen saturation or glucose level. Furthermore, "vital sign" generally includes health indications obtained from the shape of the PPG signal (e.g. shape may say something about partial arterial blockage (e.g. shape obtained from PPG signals of the hand gets more sinusoidal when applying a blood-pressure cuff on the arm), or about the skin thickness (e.g. a PPG signal from the face is different than from the hand), or maybe even about the temperature, etc.).

The term "vital sign information" as used in the context of the present invention comprises the one or more measured vital signs as defined above. Furthermore, it comprises data referring to a physiological parameter, corresponding waveform traces or data referring to a physiological parameter of a time that can serve for subsequent analysis.

For obtaining a vital sign information signal of the subject the data signals of skin pixel areas within the skin area are evaluated. Here, a "skin pixel area" means an area comprising one skin pixel or a group of adjacent skin pixels, i.e. a data signal may be derived for a single pixel or a group of skin pixels.

In still another embodiment said signal mixer is configured to use blind source separation, in particular principal component analysis or independent component analysis, to compute the at least one mixed signal. The various methods may each have advantages and disadvantages and may be selected according to the desired use.

Further, in an embodiment said signal mixer is configured to compute a single mixed signal that correlates with the at least two signal channels in a predetermined set of one or more ratios. The correlation may e.g. be computed as the inner product of the single mixed signal and the at least two signal channels. This gives two values (e.g. A and B) that, written as a normalized vector ([A, B]/norm ([A, B]) should be identical to the predetermined set of one or more ratios, e.g. the normalized blood volume vector (called "predetermined index element having a set orientation indicative of a reference physiological information" in US 2013/271591 A1 describing details of the PBV-method).

In yet another embodiment, said signal mixer is configured to compute the at least one mixed signal as a mix of at least 2 orthogonal color difference signals. For instance, R-G (red minus green) is a useful example of a color difference signal, and R+G-2*B (red plus green minus two times blue) is another useful example that is orthogonal to the first example. The background of this way of mixing has been given in G. de Haan and V. Jeanne, "Robust pulse-rate from chrominance-based rPPG", IEEE Transactions on Biomedical Engineering 2013 October; 60(10): 2878-86. The color difference signals inherently suppress the specular reflection and the mix of at least two color difference signals suppresses further motion-induced distortions in the vital sign output signal. The subsequently explained embodiments provide applications of the invention to BSS, a method using the blood-volume pulse, and a chrominance-based method.

The detector for detecting electromagnetic radiation transmitted through or reflected from a skin region of a subject and for deriving detection data from the detected electromagnetic radiation may be implemented in various ways. In one embodiment the detector comprises a plethysmography sensor configured for being mounted to a skin portion of the subject for acquiring photo-plethysmography signals. Such a sensor may e.g. be an optical plethysmography sensor mounted to a finger or earlobe or a sensor arranged within a wristband or wristwatch.

In another embodiment the detector may comprise an imaging unit for acquiring a sequence of image frames of the subject over time, from which photo-plethysmography signals can be derived using the principle of remote PPG. The data stream may thus comprise a sequence of image frames or, more precisely, a series of image frames comprising spectral information. For instance, RGB-images comprising color information can be utilized. However, also frames representing infrared (IR) and red (R) information can form the sequence of frames. The image frames can represent the observed subject and further elements.

BRIEF DESCRIPTION OF THE DRAWINGS

These and other aspects of the invention will be apparent from and elucidated with reference to the embodiments described hereinafter. In the following drawings.

DETAILED DESCRIPTION OF THE INVENTION

Figure 1:
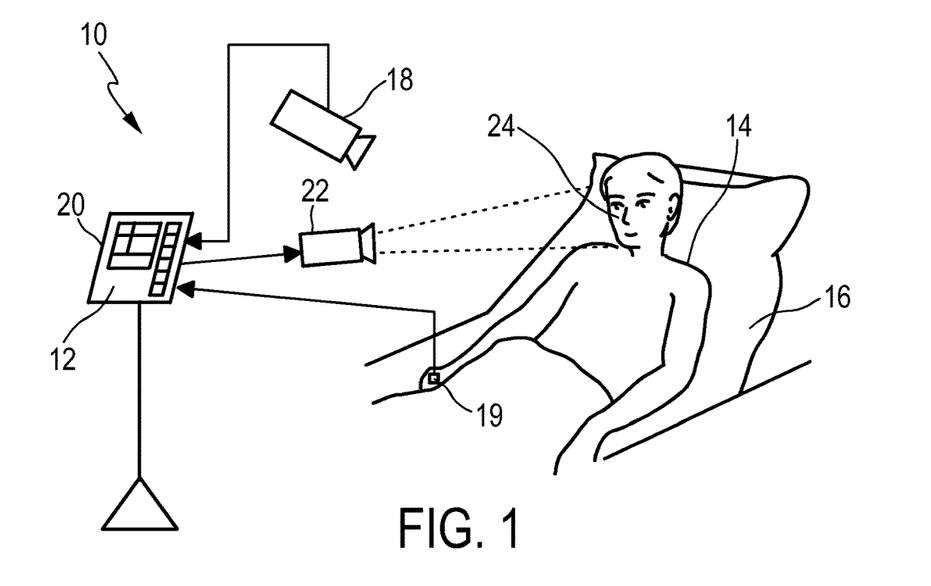
FIG. 1 shows a schematic diagram of a system according to the present invention.

FIG. 1 shows a schematic diagram of a system 10 according to the present invention including a device 12 for extracting physiological information indicative of at least one vital sign of a subject 14 from detected electromagnetic radiation transmitted through or reflected from a subject. The subject 14, in this example a patient, lies in a bed 16, e.g. in a hospital or other healthcare facility, but may also be a neonate or premature infant, e.g. lying in an incubator, or person at home or in a different environment. The subject 14, in this example a patient, lies in a bed 16, e.g. in a hospital or other healthcare facility, but may also be a neonate or premature infant, e.g. lying in an incubator, or person at home or in a different environment.

There exist different embodiments for the detector, which may alternatively (which is preferred) or together be used. In the embodiment of the system 10 two different embodiments of the detector are shown.

In one embodiment the detector comprises a camera 18 (also referred to as imaging unit, or as camera-based or remote PPG sensor) including a suitable photosensor for (remotely and unobtrusively) capturing image frames of the subject 14, in particular for acquiring a sequence of image frames of the subject 14 over time, from which photoplethysmography signals can be derived. The image frames captured by the camera 18 may particularly correspond to a video sequence captured by means of an analog or digital photosensor, e.g. in a (digital) camera. Such a camera 18 usually includes a photosensor, such as a CMOS or CCD sensor, which may also operate in a specific spectral range (visible, IR) or provide information for different spectral ranges. The camera 18 may provide an analog or digital signal. The image frames include a plurality of image pixels having associated pixel values. Particularly, the image frames include pixels representing light intensity values captured with different photosensitive elements of a photosensor. These photosensitive elements may be sensitive in a specific spectral range (i.e. representing a specific color). The image frames include at least some image pixels being representative of a skin portion of the subject. Thereby, an image pixel may correspond to one photosensitive element of a photo-detector and its (analog or digital) output or may be determined based on a combination (e.g. through binning) of a plurality of the photosensitive elements.

In another embodiment the detector comprises one or more optical photo-plethysmography sensor(s) 19 (also referred to as contact PPG sensor(s)) configured for being mounted to a skin portion of the subject 14 for acquiring photo-plethysmography signals. The PPG sensor(s) 19 may e.g. be designed in the form of a finger-clip for measuring the blood oxygen saturation or a heart rate sensor for measuring the heart rate, just to name a few of all the possible embodiments.

When using a camera 18 the system 10 may further optionally comprises a light source 22 (also called illumination source), such as a lamp, for illuminating a region of interest 24, such as the skin of the patient's face (e.g. part of the cheek or forehead), with light, for instance in a predetermined wavelength range or ranges (e.g. in the red, green and/or infrared wavelength range(s)). The light reflected from said region of interest 24 in response to said illumination is detected by the camera 18. In another embodiment no dedicated light source is provided, but ambient light is used for illumination of the subject 14. From the reflected light only light in a desired wavelength range (e.g. green light) may be detected and/or evaluated.

The device 12 is further connected to an interface 20 for displaying the determined information and/or for providing medical personnel with an interface to change settings of the device 12, the camera 18, the PPG sensor(s) 19, the light source 22 and/or any other parameter of the system 10. Such an interface 20 may comprise different displays, buttons, touchscreens, keyboards or other human machine interface means.

A system 10 as illustrated in FIG. 1 may, e.g., be located in a hospital, healthcare facility, elderly care facility or the like. Apart from the monitoring of patients, the present invention may also be applied in other fields such as neonate monitoring, general surveillance applications, security monitoring or so-called live style environments, such as fitness equipment, or the like. The uni- or bidirectional communication between the device 12, the camera 18, the PPG sensor(s) 19 and the interface 20 may work via a wireless or wired communication interface. Other embodiments of the present invention may include a device 12, which is not provided stand-alone, but integrated into the camera 18 or the interface 20.

Figure 2:
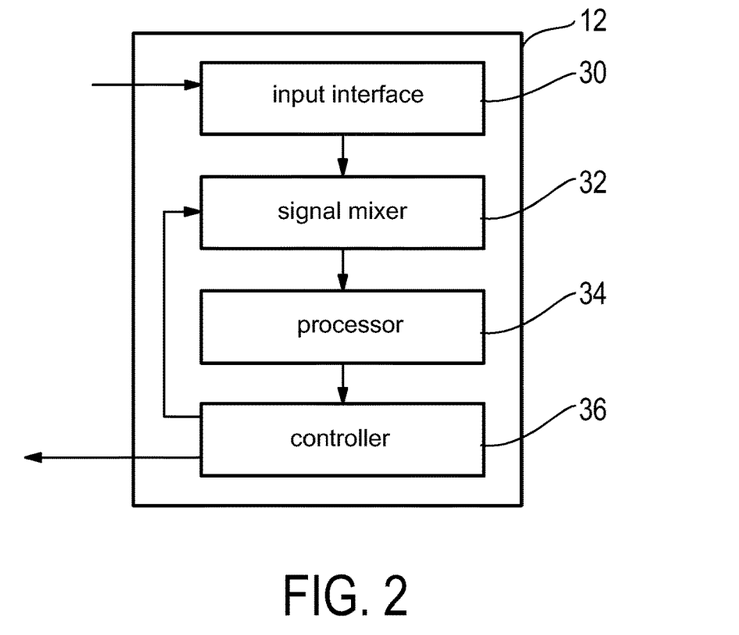
FIG. 2 shows a schematic diagram of a device according to the present invention.

FIG. 2 shows a more detailed schematic illustration of an embodiment of the device 12 according to the present invention. The device 12 comprises an input interface 30 for receiving a data stream 28 of detection data derived from detected electromagnetic radiation transmitted through or reflected from a skin region of a subject 14. The data stream of detection data is e.g. provided by the camera 18 and/or one or more PPG sensor(s) 19, and the detection data comprises wavelength-dependent reflection or transmission information in at least two signal channels representative of respective wavelength portions.

A signal mixer 32 is provided for dynamically mixing the at least two signal channels into at least one mixed signal. Various embodiments exist for said mixing which will be explained in more detail below.

A processor 34 is provided for deriving physiological information indicative of at least one vital sign from the at least one mixed signal. The way to obtain PPG signals from detected light, e.g. from images of a region of interest or from signals of a contact PPG sensor, is generally known in the field of remote or contact photo-plethymography, e.g. from the above described documents, and shall thus not be explained in more detail here.

Finally, a controller 36 is provided for controlling the signal mixer to limit the relative contributions of the at least two signal channels mixed into at least one mixed signal and/or the rate-of-change at which said relative contributions are allowed to dynamically change. In this way the reliability and accuracy of the obtained physiological information can be increased in various situations in which the conventional processing would lead to a degradation of the obtained physiological information as will also be explained in more detail below.

The various units of the device 12 may be comprised in one or multiple digital or analog processors depending on how and where the invention is applied. The different units may completely or partly be implemented in software and carried out on a personal computer connected to one or more detectors. Some or all of the required functionality may also be implemented in hardware, e.g. in an application specific integrated circuit (ASIC) or in a field programmable gate array (FPGA).

The details of the present invention shall be described for the case where the output vital sign is the pulse signal S. There exist several methods to find S, said methods being referred to as ICA, PCA, PBV, CHROM, and ICA/PCA guided by PBV/CHROM. These methods can be interpreted as providing the pulse signal as a mixture of red, green and blue signals from a color video camera, but they differ in the way to determine the optimal weighting scheme. In these methods the resulting weights are aimed at a mixture in which the distortions disappear, i.e. the "weighting vector" is substantially orthogonal to the main distortions usually caused by subject motion.

In the following some basic considerations and the essence of these methods shall be briefly explained.

The beating of the heart causes pressure variations in the arteries as the heart pumps blood against the resistance of the vascular bed. Since the arteries are elastic, their diameter changes in sync with the pressure variations. These diameter changes occur even in the smaller vessels of the skin, where the blood volume variations cause a changing absorption of the light.

Figure 3A:
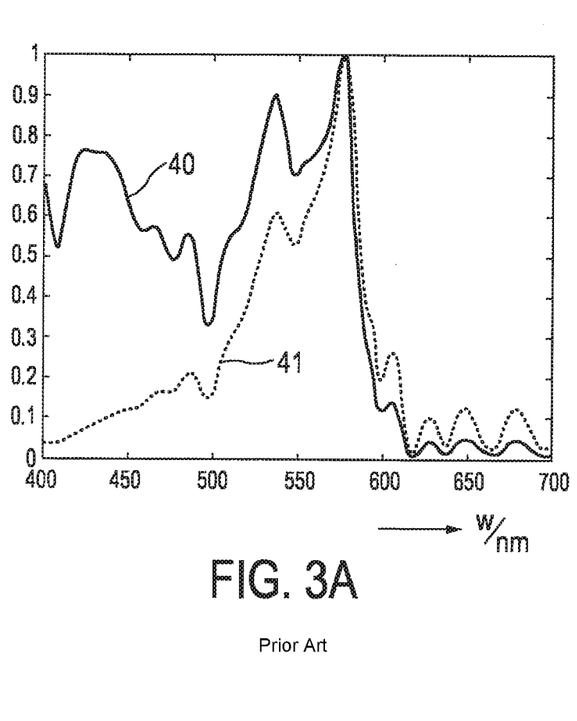
FIGS. 3A and 3B shows diagrams of the relative and absolute PPG amplitude according to two different approaches.

In M. Hülsbusch, "Ein bildgestütztes, funktionelles Verfahren zur optoelektronischen Erfassung der Hautperfusion", PhD-thesis, RWTH Aachen, 28 Jan. 2008, Fakultät für Elektrotechnik and Informationstechnik, it is explained that the resulting relative PPG amplitude is determined by the contrast between the blood and the blood-free tissue. Given the absorption spectrum of the oxygenated arterial blood and the absorption spectrum of the dermis and epidermis and assuming a concentration of 3% melanin, his simulations lead to the relative amplitude 40 as a function of wavelength as shown in FIG. 3A (also shown in the absolute amplitude 41). In this curve, the absorption peaks of oxygenated blood at 542 and 577 nm can be clearly recognized.

Figure 3B:
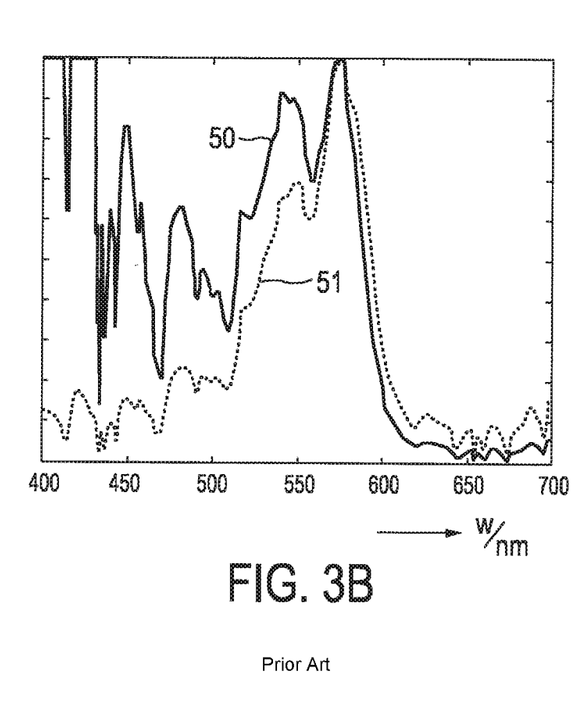

The absolute PPG-amplitude 51 as a function of wavelength was measured by Corral et al. "Optimal wavelength selection for non-contact reflection photoplethysmography", 22nd Congress of the International Commission for Optics: Light for the Development of the World, Proc. of SPIE Vol. 8011, 801191 using a spectrometer and a white, halogen, illumination. This curve 51 shows a strong amplitude peak around 550 nm, as shown in FIG. 3B. This absolute PPG, PPG(w), w being the wavelength, is related to the relative PPG-curve, RPPG(w), via the emission spectrum of the halogen illumination, I(w), and the skin-reflection spectrum, $\rho_s(w)$:

$$PPG(w)=\rho_s(w)I(w)RPPG(w). \quad (1)$$

In FIG. 3B, a derived relative PPG 50 has been included, which, apart from the higher noisiness for shorter wavelengths, corresponds reasonably well with the prediction from the model of Hülsbusch. The increased noise-level is to be expected given the weaker emission of the (halogen) lamp and the higher absorption of the skin for shorter wavelengths.

The noise-free curve from the model of Hülsbusch was used to predict the PPG-amplitude in the color channels of a regular video camera. The camera samples the visual light spectrum in a rather coarse sense using three color channels for the three primary colors of the eye, i.e. red, green and blue. These color channels are typically centered around 450 nm, 550 nm, and 650 nm, and have a relative wide bandwidth of some 100 nm and are consequently partially overlapping. Given the PPG-signal as a function of the wavelength, as predicted by the model of Hülsbusch, the relative PPG-amplitude can be predicted for different skin-tones and spectral compositions of the light source.

Figure 4A:
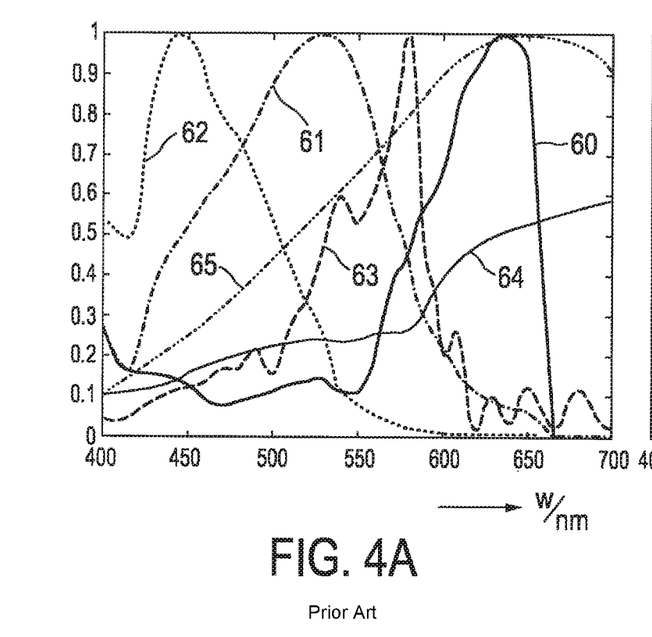
FIGS. 4A and 4B shows diagrams of input curves to the prediction of $P_{bv}$ and the relative PPG in color channels.

The unit length normalized blood volume pulse vector shall be defined as $P_{bv}$, providing the relative PPG-strength in the red, green and blue camera signal as shown in FIG. 4A. To quantify the expectations, the responses $H_{red}(w)$ (curve 60 in FIG. 4A), $H_{green}(w)$ (curve 61 in FIG. 4A) and $H_{blue}(w)$ (curve 62 in FIG. 4A) of the red, green and blue channel, respectively, were measured as a function of the wavelength w, of a global-shutter color CCD camera1, the skin reflectance 64 of a subject, $\rho_s(w)$, and used the absolute PPG-amplitude curve 63 derived from the model of Hülsbusch, PPG(w). From these curves, shown in FIG. 4A, the blood volume pulse vector $P_{bv}$ is computed as:

$$\vec{P}_{bv}^T = \begin{bmatrix} \dfrac{\int_{w=400}^{700} H_{red}(w)I(w)PPG(w)dw}{\int_{w=400}^{700} H_{red}(w)I(w)\rho_s(w)dw} \\ \dfrac{\int_{w=400}^{700} H_{green}(w)I(w)PPG(w)dw}{\int_{w=400}^{700} H_{green}(w)I(w)\rho_s(w)dw} \\ \dfrac{\int_{w=400}^{700} H_{blue}(w)I(w)PPG(w)dw}{\int_{w=400}^{700} H_{blue}(w)I(w)\rho_s(w)dw} \end{bmatrix} \quad (2)$$

which, using a white, halogene illumination spectrum I(w) 65, leads to a normalized $P_{bv}$=[0.27, 0.80, 0.54]. When using the more noisy curve measured by Corral et al. the result was $P_{bv}$=[0.29, 0.81, 0.50].

Figure 4B:
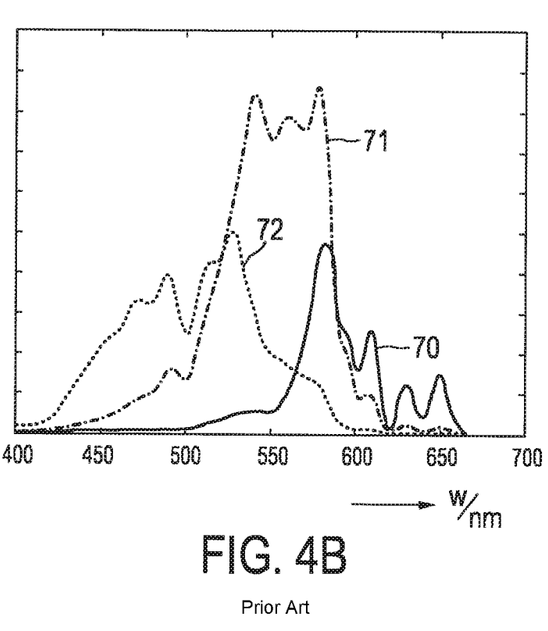

The blood volume pulse predicted by the used model corresponds reasonably well to the experimentally measured normalized blood volume pulse vector, $P_{bv}$=[0.33, 0.78, 0.53] found after averaging measurements on a number of subjects under white illumination conditions. Given this result, it was concluded that the observed PPG-amplitude, particularly in the red, and to a smaller extent in the blue camera channel, can be largely explained by the crosstalk from wavelengths in the interval between 500 and 600 nm. FIG. 4B shows how the same wavelength interval contributes to each of the camera color channels (red: 70, green: 71, blue: 72). The precise blood volume pulse vector depends on the color filters of the camera, the spectrum of the light and the skin-reflectance, as the model shows. In practice the vector turns out to be remarkably stable though. In the following this shall be verified this for a range of skin-tones.

Figure 5A:
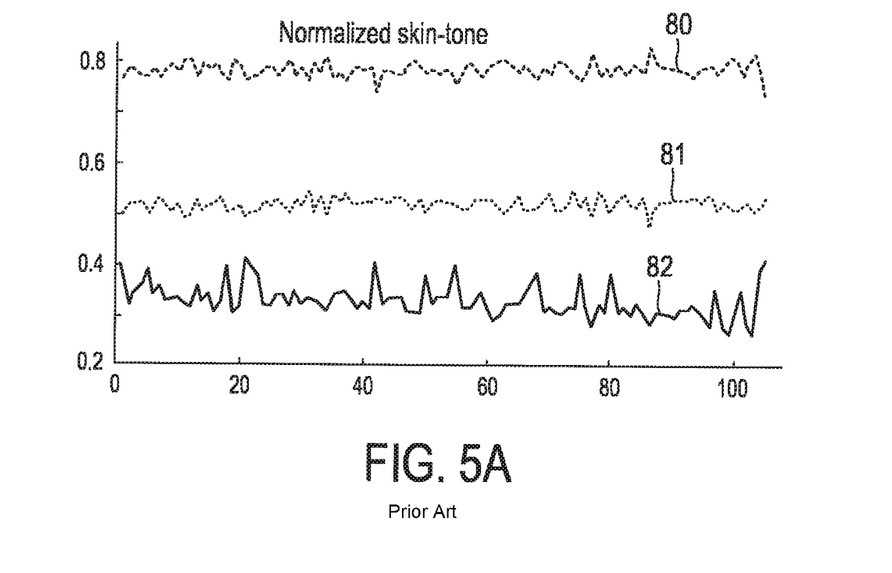
FIGS. 5A and 5B shows diagrams of normalized skin tone and $P_{bv}$ of 105 subjects.
Figure 5B:
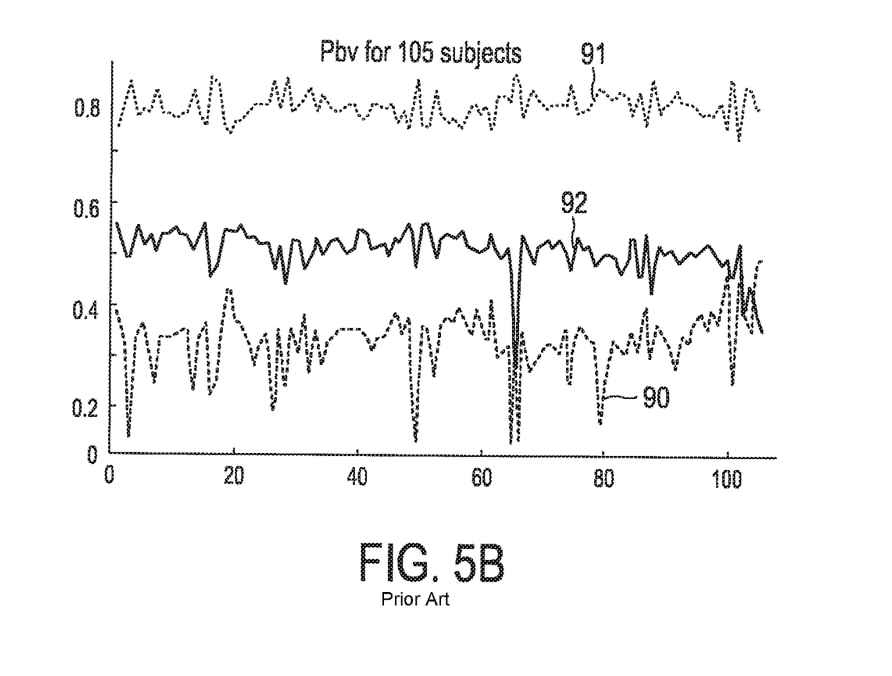

Interestingly, the relative reflectance of the skin, in the red (curve 80 in FIG. 5A), green (curve 81 in FIG. 5A) and blue channel (curve 82 in FIG. 5A) under white illumination does not depend much on the skin-type, as shown in FIG. 5A. This is likely because the absorption spectra of the blood-free skin is dominated by the melanin absorption. Although a higher melanin concentration can increase the absolute absorption considerably, the relative absorption in the different wavelengths remains the same. This implies an increase of melanin darkens the skin, but hardly changes the normalized color of the skin. Consequently, also the normalized blood volume pulse $P_{bv}$ is quite stable under white illumination. This is confirmed by FIG. 5B, showing the red (curve 90 in FIG. 5B), green (curve 91 in FIG. 5B) and blue channel (curve 92 in FIG. 5B) for the same data set of 105 subjects with different skin types.

The stable character of $P_{bv}$ can be used to distinguish color variations caused by blood volume change from variations due to alternative causes. Earlier methods to find the pulse signal from video have been described by Hülsbusch (as mentioned above), Poh et al. "Non-contact, automated cardiac pulse measurements using video imaging and blind source separation", Opt. Express 18(10), pp. 10762-10774 (2010), and Lewandowska et al. "Measuring Pulse Rate with a Webcam—a Non-contact Method for Evaluating Cardiac Activity", in Proc. FedCSIS, 2011, pp. 405-410, which are all herewith incorporated by reference. The resulting pulse signal S for all these earlier methods can be written as a linear combination (representing one of several possible ways of "mixing") of the individual DC-free normalized color channels:

$$S = W C_n \quad (3)$$

with $WW^T = 1$ and where each of the three rows of the 3×N matrix $C_n$ contains N samples of the DC-free normalized red, green and blue channel signals $R_n$, $G_n$ and $B_n$, respectively, i.e.:

$$\vec{R}_n = \frac{1}{\mu(\vec{R})} \vec{R} - 1, \quad (4)$$

$$\vec{G}_n = \frac{1}{\mu(\vec{G})} \vec{G} - 1,$$

$$\vec{B}_n = \frac{1}{\mu(\vec{B})} \vec{B} - 1.$$

Here the operator $\mu$ corresponds to the mean. Key difference between the methods is in the calculation of the weighting vector W. Hülsbusch separated the noise and the PPG signal into two independent signals built as a linear combination of two color channels. One combination approximated a clean PPG signal, the other contained noise due to motion. As an optimization criterion he minimized the energy in the pulse-signal. Poh et al. and Lewandowska et al. both proposed to use a linear combination of the three color channels to obtain the pulse signal. Poh et al. used the ICA while Lewandowska et al. used the PCA to find this linear combination. Since it is a priori unknown which weighted color signal is the pulse signal all of them used the periodic nature of the pulse signal as the selection criterion.

The above provides an explanation of the BSS method. A different approach was used by de Haan (as described in the above mentioned paper) who assumed knowledge of the orientation of distortion signals, and a constant standardized skin-color to construct a linear combination of the color signals orthogonal to the assumed distortions. This eliminated the selection based on periodicity, which was shown to be advantageous in fitness videos with periodic motion. The standardized skin-color was selected as $[R_s, G_s, B_s] = [0.7682, 0.5121, 0.3841]$ which, as can be seen from FIG. 5A, corresponds closely to actual measurements. This algorithm (CHRO), based on chrominance signals, $X_s = 0.77 R_n - 0.51 G_n$ and $Y_s = 0.77 R_n + 0.51 G_n - 0.77 B_n$, finds the pulse signal S as:

$$\vec{S} = \vec{X}_s - \alpha \vec{Y}_s, \text{ with } \alpha = \frac{\sigma(\vec{X}_s)}{\sigma(\vec{Y}_s)}, \quad (5)$$

and where the operator σ corresponds to the standard deviation. This expression can be re-written as:

$$\vec{S} = \vec{W}_{CHRO} C_n, \quad (6)$$

with $$\vec{W}_{CHRO} = \frac{1}{\sqrt{6\alpha^2 - 20\alpha + 20}} [2 - \alpha, 2\alpha - 4, \alpha]. \quad (7)$$

This rewriting makes clear that it is actually again a (differently obtained) mixture (weight vector W) of the normalized color channels (Cn).

Yet another method (called PBV-method) to obtain the mixing coefficients uses the blood volume pulse vector as basically described in US 2013/271591 A1, which is herein incorporated by reference. The best results are obtained if the band-passed filtered versions of $R_n$, $G_n$ and $B_n$ are used. According to this method the known direction of $P_{bv}$ is used to discriminate between the pulse signal and distortions. This not only removes the assumption that the pulse is the only periodic component in the video, but also eliminates assumptions on the orientation of the distortion signals. To this end, it is assumed as before that the pulse signal is built as a linear combination of normalized color signals as in Eq. (3). Since it is known that the relative amplitude of the pulse signal in the red, green and blue channel is given by $P_{bv}$, the weights, $W_{PBV}$, are searched that give a pulse signal S, for which the correlation with the color channels $R_n$, $G_n$, and $B_n$ equals $P_{bv}$ $$\vec{S} C_n^T = k \vec{P}_{bv} \Leftrightarrow \vec{W}_{PBV} C_n C_n^T = k \vec{P}_{bv},$$

and consequently the weights determining the mixing are determined by $$\vec{W}_{PBV} = k \vec{P}_{bv} Q^{-1} \text{ with } Q = C_n C_n^T, \quad (8)$$

and the scalar k is determined such that $W_{PBV}$ has unit length. It is concluded that the characteristic wavelength dependency of the PPG-signal, as reflected in the normalized blood volume pulse, $P_{bv}$, can be used to estimate the pulse signal from the time-sequential RGB pixel data averaged over the skin area. This algorithm is referred to as the PBV-method.

In the following alternatives shall be introduced to loosen the assumptions. In particular, yet four more ways are described to compute the mixing coefficients. All methods that result in such a mixing of color channels can be adapted using the present invention by modifying the weights.

A strong point of the methods based on blind source separation (BSS), like ICA and PCA, is that they do not rely on assumptions regarding the type of distortions or the orientation of skin-tone or blood volume pulse vectors. Their weak point is that it is upfront unclear which output component carries the pulse signal. It has been shown earlier by de Haan that using periodicity as the characteristic of the pulse signal for component selection leads to poor motion robustness as this requires quick adaptation to changing statistics, i.e. short overlap-add intervals with insufficient resolution in the Fourier domain. Moreover in a fitness setting substantially all motions are periodic with their frequency in the same range as the pulse rate.

As an alternative, it is proposed to use the weighting coefficients, W of Eq. (5) or (8), obtained from the CHRO- or PBV-method to guide the component selection. A good option chooses the component that has the largest (absolute)

correlation. The resulting algorithms allow a weighting that more precisely minimizes the distortions, since the assumptions—known distortions for CHRO, and stable $P_{bv}$ for PBV—are used for guidance only and small deviations play no role.

To illustrate the algorithms, it is assumed that ICA or PCA generates three component signals, S1, S2, S3 each obtained as a linear combination of the normalized RGB signals, $C_n$:

$$S_i = W_i C_n \text{ with } i=1,2,3. \quad (9)$$

Now, the pulse signal S is chosen from the component signals using a reference weight vector, $W_{REF} = W_{CHRO}$ or $W_{REF} = W_{PBV}$, obtained from the CHRO- or PBV-algorithm, equal to $S = S_p$ with $p \in \{1, 2, 3\}$ such that $$\forall_{i \in \{1,2,3\}} |\vec{W}_p \vec{W}_{REF}^T| \geq |\vec{W}_i \vec{W}_{REF}^T|. \quad (10)$$

This gives four additional algorithms, ICA, or PCA guided by CHRO, or by PBV. All algorithms may use the overlap-add processing as introduced in the above mentioned paper of de Haan, and can successfully use short interval lengths unlike the earlier BSS-based algorithms using periodicity as the component selection criterion. Since BSS cannot guarantee the polarity of the pulse signal, the sign of individual signal fragments is corrected for interval M, $S_M$, using:

$$\vec{S}_M = \text{sign}(\vec{W}_{p,M} \vec{W}_{REF,M}^T) S_{p,M}. \quad (11)$$

where p may vary from one interval to the other.

In the absence of substantial distortions, which typically means a very stationary subject, the orientation of the weighting vector (that determines the mixing of the color channels) becomes undetermined and exhibits random variations over time (usually an overlap-add procedure is applied to allow temporal adaptation of the weighting vector). These random variations cause the SNR of the resulting output pulse signal to be significantly worse than the SNR obtained with (limited) distortions present.

In a first embodiment of the present invention applying the above explained CHRO-method, the observation is used that in most cases the distortions have a known direction in normalized RGB-space. Motion typically translates mostly in intensity variations, i.e. distortions in the direction [1 1 1]. To eliminate this distortion the weighting vector W is expected to lie in the chrominance plane, i.e. sum(W) is close to zero. In this first embodiment the weighting vector W is replaced by a default vector. A good exemplary choice is Wd=[−1 1.4 −0.4] or Wd=[−1 2 −1]) whenever sum(W) exceeds a threshold.

A second common distortion is due to specular reflections, which typically causes the saturation of the color to change but not the hue. In the second embodiment, therefore the weight vector W is limited to a range around the vector orthogonal to intensity and saturation, i.e. W is limited to a range (fixed angle) around the earlier mentioned default vector Wd.

Applying the CHRO-method another good embodiment clips the value of $\alpha$ (see eq. (5)) between 0.8 and 1.2.

In a further preferred embodiment the above limitations are only activated in case the problem is likely, i.e. has a likelihood of existence above a likelihood threshold. This can be estimated e.g. by the standard deviation of the color signals, or a chrominance signal, the eigenvalues in a PCA-based method, or the norm of the covariance matrix, Q, of the PBV-method (see eq. (8)).

A drawback of the described embodiments may be that the limitation choice is based on the most common distortion. This could be suboptimal is particular cases. To improve this aspect, a preferred embodiment computes the "default" weighting vector Wd by updating the aforementioned default vector every time a signal segment is encountered that seems to have a near optimal level of distortion as explained below. In a further elaborated version of this embodiment the default weighting vector Wd results from a recursive process: Wd(new)=0.01×W(reliable)+0.99×Wd (old), where W(reliable) is a weighting vector obtained during the most recent signal portion with near optimal level of distortion using the method to be improved. In case the method to be improved is the PBV-method, again the norm of Q can be used to select W(reliable). A very high norm usually implies unreliable W due to excessive distortion and a very small norm implies an unreliable W due to absence of distortion, so an intermediate value suggests updating Wd. In case the method to be improved is the CHRO method, the norm of Y can be used instead. Again a very high norm usually implies unreliable mixing due to excessive distortion and a very small norm implies an unreliable $\alpha$ (and hence W) due to absence of distortion, so an intermediate value suggests updating $\alpha$.

In the above description, extraction of the vital sign is assumed from a single color value for the skin at a given moment in time (global method). It is known that more advantageous methods may subdivide the skin region into various sub-regions and derive multiple candidate vital sign signals from these sub-regions that can be combined adaptively into the output vital sign signal (representing a local method, as e.g. described in yet unpublished European patent application 12 199 139.2, which is herein incorporated by reference). In this case two or more of the above mentioned embodiments may be used in parallel. However in this case, that the preferred embodiment may also use a common default weighting vector Wd that can be recursively updated by all spatial regions that are assumed "reliable" (e.g. non-extreme covariance matrix).

The invention aims at improving the performance of rPPG and PPG algorithms for situations where the level of distortions is very low (near stationary subject). In this case the weighting vector becomes poorly defined and a SNR results that is a lot worse than what one would expect for such an "easy" case. Preferably, the limits have been fixed and experimentally optimized to provide a good SNR. Since "limiting" showed to be less good than limiting the rate-of-change (e.g. by recursive low-pass filtering), most effort has been focused on that option.

The relative contributions can be limited by clipping the value of variable $\alpha$, obtained from equation 5, between the values 1.2 and 0.8, leading to a valuable improvement. This improvement got even better when the variable $\alpha$=1, in case equation 5 resulted in a value outside the range <0.8, 1.2>. In another attempt, the sum of the weight vector (for mixing) W obtained for any method was checked using the covariance matrix Q. If this sum deviated substantially from 0, while the norm of Q was low, the computed W can be replaced with a fixed weighting vector W=[−0.4 0.8 −0.4]. The rate of change can be limited by replacing the weighting vector W by a recursively filtered version W(used)=0.01× W(reliable)+0.99×Wd(old).

Results (spectrograms) obtained from various body locations show that the pulse signal becomes a lot cleaner with the modification proposed according to the present invention. Also it can be seen that pulse signal present in the motion of clothing, e.g. a shirt, is being suppressed after the modification as it does not exhibit the typical color variation expected in skin.

A local method as mentioned above is generally expected to be less sensitive to noise, as individual noisy results are averaged. Nonetheless, experimental results show a significant improvement (more than 1 dB in SNR), even though sequences were tested that contained hundreds of sub-regions in a large skin area.

Further, a movie shot at the NICU of a neonate shows clear improvement, i.e. the motion artifacts, in this case due to respiratory motion in a colored environment, are significantly reduced (though not completely eliminated).

The above described methods have mainly been explained with respect to contactless sensors. Generally, the same methods can also be used for contact sensors. For CHRO and ICA/PCA guided by CHRO three wavelengths would be required. The other methods can also work with only two wavelengths.

By way of example, the present invention can be applied in the field of health care, e.g. unobtrusive remote patient monitoring, general surveillances, security monitoring and so-called lifestyle environments, such as fitness equipment, or the like. Applications may include monitoring of oxygen saturation (pulse oximetry), heart rate, blood pressure, cardiac output, changes of blood perfusion, assessment of autonomic functions, and detection of peripheral vascular diseases. The present invention can e.g. be used for rapid and reliable pulse detection of a critical patient, for instance during automated CPR (cardiopulmonary resuscitation). The system can be used for monitoring of vital signs of neonates as well. In summary, the present invention improves the SNR considerably for near stationary subjects and consequently leads to a more accurate beat-to-beat measurement.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or an does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Furthermore, the different embodiments can take the form of a computer program product accessible from a computer usable or computer readable medium providing program code for use by or in connection with a computer or any device or system that executes instructions. For the purposes of this disclosure, a computer usable or computer readable medium can generally be any tangible device or apparatus that can contain, store, communicate, propagate, or transport the program for use by or in connection with the instruction execution device.

In so far as embodiments of the disclosure have been described as being implemented, at least in part, by software-controlled data processing devices, it will be appreciated that the non-transitory machine-readable medium carrying such software, such as an optical disk, a magnetic disk, semiconductor memory or the like, is also considered to represent an embodiment of the present disclosure.

The computer usable or computer readable medium can be, for example, without limitation, an electronic, magnetic, optical, electromagnetic, infrared, or semiconductor system, or a propagation medium. Non-limiting examples of a computer readable medium include a semiconductor or solid state memory, magnetic tape, a removable computer diskette, a random access memory (RAM), a read-only memory (ROM), a rigid magnetic disk, and an optical disk. Optical disks may include compact disk-read only memory (CD-ROM), compact disk-read/write (CD-R/W), and DVD.

Further, a computer usable or computer readable medium may contain or store a computer readable or usable program code such that when the computer readable or usable program code is executed on a computer, the execution of this computer readable or usable program code causes the computer to transmit another computer readable or usable program code over a communications link. This communications link may use a medium that is, for example, without limitation, physical or wireless.

A data processing system or device suitable for storing and/or executing computer readable or computer usable program code will include one or more processors coupled directly or indirectly to memory elements through a communications fabric, such as a system bus. The memory elements may include local memory employed during actual execution of the program code, bulk storage, and cache memories, which provide temporary storage of at least some computer readable or computer usable program code to reduce the number of times code may be retrieved from bulk storage during execution of the code.

Input/output, or I/O devices, can be coupled to the system either directly or through intervening I/O controllers. These devices may include, for example, without limitation, keyboards, touch screen displays, and pointing devices. Different communications adapters may also be coupled to the system to enable the data processing system to become coupled to other data processing systems, remote printers, or storage devices through intervening private or public networks. Non-limiting examples are modems and network adapters and are just a few of the currently available types of communications adapters.

The description of the different illustrative embodiments has been presented for purposes of illustration and description and is not intended to be exhaustive or limited to the embodiments in the form disclosed. Many modifications and variations will be apparent to those of ordinary skill in the art. Further, different illustrative embodiments may provide different advantages as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated. Other variations to the disclosed embodiments can be understood and effected by those skilled in the art in practicing the claimed invention, from a study of the drawings, the disclosure, and the appended claims.

The invention claimed is:

1. A device for extracting physiological information indicative of at least one vital sign of a subject from detected electromagnetic radiation transmitted through or reflected from the subject, said device comprising:

a detector configured to detect electromagnetic radiation transmitted through or reflected from a skin region of the subject;

an input interface configured to:
- receive a data stream of detection data derived from detected electromagnetic radiation from the detector, wherein the detection data comprises wavelength-dependent reflection or transmission information in a red color channel, a blue color channel, and a green color channel; and
- receive a motion signal indicating motion of the subject or part of the subject measured by accelerometers attached to the patient;

a signal mixer configured to dynamically mix the red, blue, and green channels into at least one mixed signal, a processor configured to derive physiological information indicative of at least one vital sign from the at least one mixed signal, a display configured to display the derived physiological information, and a controller configured to:
- control the signal mixer to limit the relative contributions of each of the red, blue, and green channels mixed into the at least one mixed signal during the mixing in case the motion indicated by the motion signal is below a motion threshold to improve the signal to noise ratio of the derived physiological information indicative of at least one vital sign; and
- limit the rate-of-change at which said relative contributions are allowed to dynamically change during the mixing in case the motion indicated by the motion signal is below the motion threshold to improve the signal to noise ratio of the derived physiological information indicative of at least one vital sign.

2. The device as claimed in claim 1, wherein the controller is configured to limit the relative contributions and/or their rate-of-change when the energy of one or more of the red, blue, and green channels or a derived measure is below an energy threshold.

3. The device as claimed in claim 1, wherein the controller is configured to limit the relative contributions and/or their rate-of-change to a predetermined value or range.

4. The device as claimed in claim 1, wherein said controller is configured to limit the rate-of-change by updating the relative contributions.

5. The device as claimed in claim 1, wherein said signal mixer is configured to use blind source separation to dynamically mix the at least one mixed signal.

6. The device as claimed in claim 1, wherein one of the mixed signals correlates with the red, blue, and green channels in a predetermined set of one or more ratios, the correlation being computed as an inner product of the mixed signal and at least two of the red, blue, and green channels.

7. The device as claimed in claim 1, wherein said signal mixer is configured to dynamically mix the at least one mixed signal from red, blue, and green orthogonal color difference signals, the mixed signal being mixed by subtracting the green channel from the red channel to obtain a first color difference signal, and adding the red and green channels and subtracting two times the blue channel to obtain a second color difference signal orthogonal to the first.

8. The device as claimed in claim 1, wherein said detector comprises a plethysmography sensor configured for being mounted to a skin portion of the subject for acquiring photo-plethysmography signals and/or a camera for acquiring a sequence of image frames of the subject over time, from which photo-plethysmography signals can be derived.

9. The device as claimed in claim 4, wherein said controller is configured to limit the rate-of-change by recursively updating the relative contributions.

10. The device as claimed in claim 5, wherein said signal mixer is configured to use principal component analysis or independent component analysis to dynamically mix the at least one mixed signal.

* * * * *